United States Patent [19]
Dear et al.

[11] Patent Number: 4,943,358
[45] Date of Patent: Jul. 24, 1990

[54] OXIDATION PROCESS

[75] Inventors: Kenneth M. Dear, Great Sutton; Philip J. Turner, Widnes, both of England

[73] Assignee: Interox Chemicals Limited, London, United Kingdom

[21] Appl. No.: 323,976

[22] Filed: Mar. 15, 1989

[30] Foreign Application Priority Data

Mar. 19, 1988 [GB] United Kingdom ................ 8806583

[51] Int. Cl.$^5$ ............................................. B01J 19/08
[52] U.S. Cl. .......................... 204/157.93; 204/157.97; 204/157.99; 204/158.1
[58] Field of Search ...................... 204/157.93, 157.97, 204/157.99, 158.1

[56] References Cited

U.S. PATENT DOCUMENTS 4,165,268  8/1979  Marti .............................. 204/157.99
4,191,621  3/1980  Riethmann ..................... 204/157.99

OTHER PUBLICATIONS

G. E. Robinson and J. M. Vernon, "Photochemical Phenylation and Oxidation of Halogen-Substituted Diphenylmethanes in Benzene", *J. Chem. Soc.*, (C), 1979, pp. 2586–2591.

Primary Examiner—John F. Niebling
Assistant Examiner—Ben C. Hsing
Attorney, Agent, or Firm—Larson and Taylor

[57] ABSTRACT

It is desired to find an alternative way to produce benzophenones or substituted benzophenones which does so selectively and avoids the problems of previous methods that use, for example, large amounts of an aluminium chloride catalyst or nitric acid.

In the invention process, a diphenyl methane starting material (DPM) in a hydrophobic phase is oxidized in a photolytic process by contact with an aqueous phase containing greater than 1 mole of HBr and at least 1.5 moles of $H_2O_2$, both per mole of DPM, the radiation being capable of dissociating bromine to its radicals, and especially using light of wavelength 600 to 250 nm. Preferably, a reaction temperature of around 50° to 65° C., is used, the organic solvent comprising a suitably boiling chlorinated carbon or hydrocarbon. The $H_2O_2$ is introduced progressively into the reaction mixture. The benzophenone product is recovered substantially in the organic phase, whereas most of the bromine/bromide is retained in the aqueous phase which can be re-employed in a subsequent oxidation of DPM, possibly after restoration of the bromide to its initial concentration.

In a modification to the process, by suitably controlling the mole ratios of bromide and $H_2O_2$ to DPM at about 1:1:1, and preferably using a reaction temperature of about ambient to 35° C., the DPM can be substituted by a single bromine atom on the methane carbon also with good selectively, instead of being oxidized to the benzophenone.

27 Claims, No Drawings

OXIDATION PROCESS

The present invention relates to an oxidation process and in particular to the oxidation of a methylene group to a carbonyl group.

Carbonyl compounds can often be of value as chemical intermediates, one class of which comprises benzophenone and various substituted benzophenones. A traditional route for preparing benzophenones employs a Friedel-Crafts reaction, for example between benzene and benzoyl chloride. The route however requires a very substantial amount of a catalyst, anhydrous aluminium chloride, often a stoichiometric amount, which is consumed upon isolation of the benzophenone. Accordingly, an alternative production route has been sought. The corresponding diphenyl substituted methane compounds of at least some of the benzophenones are readily available, and in theory it would be possible to oxidise them to the ketone. One reagent that has been employed comprises nitric acid, but processes based on that reagent suffer from the disadvantage of emissions of nitrogen oxides that need to be controlled, amongst other reasons.

A process for bromine-catalysed photo-oxidation of diphenylmethanes in air has been suggested by G. E. Robinson and J. M. Vernon in a paper in the Journal of the Chemical Society, 1970, pp 2586 to 2591. The authors showed that the addition of an equimolar amount of bromine to the reaction medium improved substantially the rate of conversion of diphenylmethane to reaction products when the medium was irradiated using a low pressure mercury arc lamp in an oxidising atmosphere, air. One of the products was benzophenone, but at a selectivity of production of only 56%, which is acceptable for a laboratory demonstration, but is impractical for commercial production. A slightly better selectivity was attained for conversion of a substituted diphenylmethane. When a lower mole ratio of bromine to substrate of 0.2:1 was employed, the proportion of substrate converted to product was much reduced to 21.8%, even though a 5 times longer reaction period was used. The authors sought to explain their results by a reaction mechanism, but the corroborative tests that they themselves proposed failed to yield support for their mechanism, so that it is open to some doubt. In consequence, there is no simple guidance deducible from the text as to how to improve selectivity.

It is an object of the present invention to provide an alternative or improved process for the production of benzophenones that avoids or mitigates the disadvantages of the processes outlined hereinabove.

In the course of devising the instant invention, the inventors found that it was possible to control a photolysis process employing bromine generated in situ so as to improve selectivity of production of the various reaction products that were found to be obtained, including specifically a method of obtaining the benzophenone selectively or bromine substitution selectively.

According to the present invention there is provided a process for the oxidation of a diphenyl methane to the corresponding benzophenone in which process a diphenyl methane compound in a hydrophobic solvent is reacted with bromine whilst irradiating with light of a sufficiently short wavelength to generate bromine radicals from the bromine, characterised in that the diphenyl methane compound is selected from compounds having the general formula

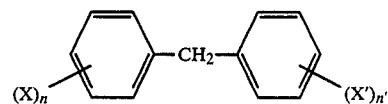

in which X and X' each represents independently a halogen or sulpho or nitro group or a phenyl group, and n and n' each is an integer from 0 to 3, and the reaction medium comprises an aqueous phase in addition to the hydrophobic phase, said aqueous phase containing HBr and $H_2O_2$ at concentrations sufficient to generate bromine in solution, and further characterised in that the amount of HBr present is greater than equimolar to the diphenyl methane compound, and in that the total amount of hydrogen peroxide introduced into the reaction medium and reacted therein is at least approximately 1.5 moles per mole of the diphenyl methane.

By the use of a process according to the present invention as aforementioned, there are several additional benefits of a practical nature in addition to substantial benefit of improved selectivity. These benefits which will be given in more detail later, include the avoidance of supply of bromine as such, the avoidance of excessive consumption of bromine and the capability of re-employing the bromidic reactant to carry out the ketone generation for a plurality of reactions, thereby also minimising the problems of waste disposal of aqueous bromide and separating a mixture of reaction products.

Within the general formula for the starting material, n and/or n' can be 0, in which case that particular phenyl group is unsubstituted, but when n or n' is 1 or more, it will be understood that X and X' each can, at the discretion of the user be ortho, meta or para to the bridging methylene group. Particularly good results have been achieved already when the substituent X and/or X' is in the para position, and when there is no substitution. It is often particularly convenient to employ symmetrical starting materials, i.e. when both n and n'=0 or when both n and n'=the same integer and X represents the same substituent as X' and in the same position around the benzene nucleus as each other. That convenience arises from the greater availability of symmetrical compounds, and not from considerations of differences in reactivity in the instant invention process. It will accordingly be further recognised that the invention process is directly applicable to asymmetrical starting materials as well, i.e. when X represents one substituent, and X' represents a different substituent or when one of the phenyl groups is unsubstituted. The number n/n' of substituents X and X' is each often 1, but starting materials with n and/or n' greater than 1 also can be employed. Amongst the possibilities for X and X', specific mention is appropriate for chloro and fluoro substituents which remain substantially the same at the end of the reaction, i.e. in the same positions around the benzene nucleus and not replaced by a bromo or other substituent, and similarly X and/or X' can represent other deactivating groups namely sulpho or nitro groups. X and/or X' can represent also a phenyl substituent and for the avoidance of doubt such a phenyl substituent can itself also be substituted by a halogen, sulpho or nitro group or groups.

Herein, the diphenylmethane compounds that are suitable for use in the present invention are sometimes represented by the abbreviation DPM.

It is desirable to employ in the hydrophobic phase a solvent for DPM. This solvent is often a liquid hydrocarbon or halogenated (especially chlorinated) hydrocarbon, the term including those compounds in which all the hydrogen atoms have been replaced by halogen, and especially chlorine atoms. One presently preferred solvent is chloroform but others such as ethylene dichloride, carbon tetrachloride, tetrachloroethylene, tetrachloroethane and dichloromethane are useful alternatives, and the selection of solvent, though at the discretion of the user, will in many instances take into account the desirability of employing one that has a boiling point somewhat higher than the desired operating temperature. Mixtures of the organic solvents are usable also. Those hydrocarbon fractions or halogenated hydrocarbon solvents or mixtures thereof are preferred which have boiling points of at least 50° C. The concentration of DPM reactant in the organic solvent is often from 100 to 300 g/l.

It will be recognised that the reaction between hydrogen peroxide and hydrogen bromide can occur readily in an aqueous medium and complements the reactions between the diphenylmethane compound and bromine which the inventors believe eventually regenerates hydrogen bromide. There is, accordingly, provided a mechanism for ameliorating or circumventing simultaneously the problems of supply of bromine liquid and disposal of hydrogen bromide-containing effluent, neither supply nor disposal being necessary in a recycle process in which the effluent is retained for reuse to make further product, possibly after concentration.

It has been found, in practice that the overall amount of hydrogen peroxide that is introduced, primarily for the generation of bromine is at least 1.5 moles per mole of diphenylmethane and especially is about 2 moles or more per mole of DPM, in order to optimise the selectivity of the production of the desired ketone as product. The relevant reaction for generating bromine is:

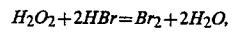

$H_2O_2 + 2HBr = Br_2 + 2H_2O$, i.e. one mole of hydrogen peroxide theoretically can generate one mole of bromine. Accordingly, it might be expected that the amount of bromide to include in the reaction mixture is twice the molar amount of hydrogen peroxide, i.e. at least 3 moles of HBr per mole of DPM, but it has been found that there is no need for all of the bromine to be generated at once nor for all to be generated before the Br/DPM reaction commences. Accordingly, a substantially lower amount of hydrogen bromide can be employed and it is believed that the same bromide is effectively recycled in situ through a plurality of oxidations. There appears to be, however, a requirement that there is at least some excess HBr above the ratio of HBr:DPM of 1:1 in order to allow selective production of the desired ketone to be obtained. In practice, it is convenient to use at least 1.2 moles of HBr and preferably at least 1.5 moles HBr per mole DPM. Very good results have been obtained when using mole ratios of about 2:1 to about 3:1 HBr:DPM. Although a higher mole ratio could be used, it is generally not above 5:1.

The amount of hydrogen peroxide introduced is usually less than 5 moles per mole DPM, and good results often use about 2 to 2.5 moles:mole DPM.

The present invention has been described for convenience in the context of charging with HBr, but it is not necessary to introduce HBr as such into the reaction mixture. Instead, it can be formed in situ by acid displacement, using a charge of a strong acid such as sulphuric acid and a bromide salt such as ammonium bromide. Alternatively, the initial charge may comprise bromine itself, for example in the range of 0.6 to 1.0 moles per mole of DPM, which can react with the DPM and generate bromide in situ. The requirement of peroxide for oxidising the bromide would correspondingly be reduced, and accordingly in practice peroxide addition would preferably be 0.6 to 1 mole per mole DPM less per mole of bromine employed as such.

It will be recognised that at the end of the reaction period there will be two phases when the hydrogen peroxide/HBr/Br$_2$ cycle is used, and that the aqueous phase will contain a very high proportion of the residual amount bromide. This aqueous phase, after separation from the product, is available for use subsequently with a fresh batch of DPM and hydrogen peroxide. However, since in each cycle water is produced from hydrogen peroxide and extra water is normally introduced with the hydrogen peroxide, the aqueous phase gains water and thus it inevitably becomes more dilute, so that it prudent to supplement the HBr concentration on each cycle or at least periodically. The manner of increasing the bromide concentration in the aqueous phase is at the discretion of the user, most conveniently by restoring it to its concentration of the preceding cycle. Indeed, if the ratio of HBr:DPM is substantially in excess of 2:1, total restoration of HBr concentration may not be necessary every time, but only at intervals. Convenient methods can include simply discarding a fraction of the aqueous phase and adding fresh bromide to the residue, or processes for dewatering the aqueous phase, such as by refluxing the aqueous phase with a solvent such as dichloromethane so as to co-remove the solvent and water.

The desired diphenyl ketone product is sufficiently soluble for all or a substantial fraction of it to remain in solution from which it can be separated by solvent evaporation.

It is convenient to employ the organic to aqueous phases in a volume ratio in the range of about 3:1 to 1:1, and particularly around 2:1.

The aqueous phase contains also the hydrogen peroxide, which is normally introduced as an aqueous solution having a concentration of at least 35% and preferably at least 50% w/w solution. To reduce the amount of added water, a concentration of above 75% w/w H$_2$O$_2$ would be usable, such as grades containing about 85% w/w H$_2$O$_2$, but its use is not necessary and on a large scale would be hindered by its higher cost and by regulations causing transport difficulties. In practice, therefore, the most attractive compromise employs around 65% to 70% w/w H$_2$O$_2$. The hydrogen peroxide could be introduced in a variety of schemes varying from multi-shot to continuous addition throughout. In practice, it is beneficial and convenient for H$_2$O$_2$ to be added progressively during the early part of the reaction period, that is to say incremental addition at intervals or slow continuous addition during a period of from about 5 minutes to 60 minutes, representing often but not exclusively a fraction of from about 5 to 60% of the reaction period.

The radiation illuminating the reaction has as its object the dissociation of bromine into bromine radicals.

Thus, the effective radiation has a wavelength of not more than 600 nm. A significant proportion of useful radiation is available from lamps which have principal emissions in the range of 600 to 250 nm. Lamps which are described as daylight lamps have been found particularly suitable for the instant invention since the greater part of their radiation is emitted within the preferred wavelength range. Suitable lamps are often described as high pressure sodium discharge lamps (SON), mercury fluorescent lamps (MBF) and tungsten or tungsten halogen lamps. It will be recognised that there is a relationship between effective radiation intensity and reaction rate and consequently also with reaction period, the more intense the radiation, the faster the rate and shorter the reaction period needed to achieve the desired generation and utilisation of the brominaceous oxidant. It will also be understood that the actual design of the apparatus employed will contribute significantly to the efficiency which the radiation can be deployed, and relevant design factors include such factors as the ratio of reaction volume to illuminated surface area. The actual design of the reaction vessel is within the control of the process operator. Radiation lamps can for example be positioned above the surface of the reaction mixture and/or immersed within it. Alternatively or additionally the vessel can be provided with translucent ports through which the radiation is shone into the reaction mixture. Reflectors can be used to minimise radiation losses. By way of illustration, it has been found that successful results are attainable if the illuminance is selected in the range of $5 \times 10^4$ to $5 \times 10^6$ lux, and conveniently in the region of about $5 \times 10^5$ lux. However, other apparatus may permit different illuminance levels to be employed successfully.

The reaction period is normally selected within the range of 0.5 to 10 hours and in many instances is from 1 to 3.5 hours, so as to permit the progressive and controlled introduction of hydrogen peroxide and to take into account the illuminance employed. In consequence, the light exposure, which is the product of illuminance and exposure time is selected often in the range of at least $1-5 \times 10^5$ lux-hours such as up to $5 \times 10^6$ lux hours, but depends at least in part on the apparatus. Obviously, greater light exposure (as measured in lux hours) is employable but at additional expenditure. As a matter of practice, it is convenient in order to obtain the highest DPM conversion to monitor for bromine and to allow the reaction to continue whilst bromine is present. Its presence can be monitored visually or automatically, by virtue of the distinctive colour it imparts to the reaction mixture and the colour loss signals the reaction end. It will be recognised that such a procedure can advantageously be adopted, irrespective of the actual apparatus used.

The temperature of the reaction mixture can be selected in the range of 5° to 100° C., and in many operations will be from ambient (regarded as about 20° C.) up to 65° C. The choice of a higher instead of a lower temperature is preferable so as to favour the reaction sequence resulting in the ketone rather than the sequence resulting in bromine substitution. Surprisingly, in a simple modification of the process described hereinabove, and using the same apparatus, it is possible to produce products in which the DPM has been bromine substituted at its methylene carbon atom, together with only a small fraction of ketone. This fact has lead the instant inventors to conclude that the production of ketone may procede via an intermediate that is either brominated or capable of reacting to yield either the ketone or the bromine-substituted product. In view of their results, they have also concluded that the reaction sequence proposed by Robinson and Vernon for the photolytic oxidation of diphenylmethanes using bromine in the presence of oxygen at best represents a sequence that is incomplete in significant aspects and in particular omits any mechanism for bromine substitution or alternatively is of no applicability to a process using hydrogen peroxide and hydrogen bromide. In this process modification, the essential difference resides in the control of the mole ratios of respectively hydrogen peroxide and hydrogen bromide to the DPM, optimally to the vicinity of about 1:1:1. It will be recognised that in such conditions the amount of bromine produced will be in total about 1 mole per mole of DPM, although it can obviously not be produced all at once, and that this is the same overall ratio of bromine to DPM employed by Robinson and Vernon, who achieved a markedly different product mix, namely about half conversion to the ketone and the rest not fully identified, whereas in the instant modification process, the product at ambient temperature is that in which the methylene group has been brominated at a selectivity of well over 90%. Self-evidently, therefore, under the reaction conditions of such a process there is a significant and practical difference in the overall result between introduction of bromine as such and its progressive generation in situ from HBr and $H_2O_2$.

Thus, according to the process modification, there is provided a process for the conversion of a diphenylmethane in which the methane compound in a hydrophobic solvent is reacted with bromine whilst being irradiating with light of a sufficiently short wavelength to generate bromine radicals from the bromine, characterised in that the diphenyl methane compound is selected from compounds having the general formula

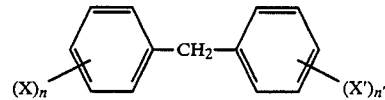

in which each of X and X' represents independently a halogen, sulpho or nitro group or a phenyl group, and n and n' each is an integer from 0 to 3, and the reaction medium comprises an aqueous phase in addition to the hydrophobic phase, said aqueous phase containing HBr and $H_2O_2$ at concentrations sufficient to generate bromine in solution, the amount of HBr and the total amount of hydrogen peroxide that is introduced into the reaction medium and consumed therein each being approximately equimolar to the diphenyl methane, whereby the diphenyl methane compound is converted mainly to the corresponding diphenyl bromomethane compound.

It will be recognised that the major difference between the process which selectively generates the ketone and the process which selectively generates the bromine-substituted compound resides in the total amount of bromine that can be generated in the reaction medium. In the bromine-substitution process, the amount is tailored to allow one atom of bromine to substitute into the substituted methane group, whereas in the ketone-producing process it is essential to have an excess amount of HBr and $H_2O_2$ present so as to encourage a further reaction which incidentally liberates the bromide for reuse. Whilst the aforementioned explanation is believed to account for the difference in products achievable by control of the relative additions of the components of the reaction mixture, it is provided solely to assist the reader to understand the various reaction steps that may occur and why the invention processes can obtain products selectively. The invention is not dependent upon the absolute veracity of the explanation.

It will be recognised that in the process modification, the starting materials are chosen from the same class of DPM as for the ketone-generating process. The choice of organic solvent, the ratio of aqueous to organic phases, the reaction periods, manner of addition and addition periods of hydrogen peroxide and reaction temperature range can be chosen from within the same ranges as for the ketone-producing process. However, it is preferable for the reaction temperature to be controlled to the lower part of the range, such as to below 35° C., so as to improve selectivity to the bromine-substitution relative to ketone formation.

Having described the invention in general terms, specific embodiments thereof will now be described in greater detail by way of example.

In each of Examples 1 to 9 and comparisons CA, CB and CC and Examples of the modified process M10 and M11, the reaction was carried out in a multi necked 200 ml glass flask equipped with stirrer, thermometer and inlet port through which reagent can be introduced. The diphenyl methane compound identified in the Table (DPM) was dissolved in an organic solvent, (100 mls of chloroform except for Ex 1 when it was 200mls and Example M11 in which it was dichloromethane) with agitation at about 30° C. in the flask. The organic solution was then mixed with an aqueous 62% w/w solution of HBr in an amount specified in the Table.

The reaction mixture was brought, where necessary, to the reaction temperature and the desired amount of aqueous hydrogen peroxide (70% w/w) was then introduced slowly and progressively into the flask with stirring over a period of about 20 minutes except in Example 1 when it was about 1 hour, as specified in the Table. During the remainder of the reaction period, no further peroxide was introduced, but the reaction continued to be stirred and maintained at the selected temperature until the red-brown colour attributable to bromine had disappeared.

Throughout the reaction period except in comparison CA, the flask was irradiated by a daylight spectrum lamp positioned about 15-25 cm away and shining a beam onto the mixture. The lamp employed was a Thorn Al/258 24 volt 250 watt lamp, having a nominal luminous flux of 8500 lumens.

At the end of the reaction period, the reaction mixture was cooled to ambient temperature and the lower organic phase was run off. The aqueous residue was then washed twice with its own volume of fresh organic solvent, usually chloroform, and the washings combined with the organic phase. Solvent was stripped off at reduced pressure yielding a solid product which was analysed by capillary gas chromatography.

In comparison CA, the reaction was carried out without any illumination in a darkened room.

In many of the Examples or comparisons, the product was not analysed for the corresponding diphenyl bromomethane and this is designated in the Table by nm.

The diphenyl methane compounds employed as starting materials were as follows:

| | |
|---|---|
| diphenyl methane | Ex 1, CB, M10, M11 |
| 4,4'-difluorodiphenyl methane | Ex 2, Ex 3, Ex 8, Ex 9, CA, and CC |
| 4,4'-dichlorodiphenyl methane | Ex 4 |
| 4-phenyldiphenyl methane | Ex 5 |
| 4-chlorodiphenyl methane | Ex 6 |
| 4-fluorodiphenyl methane | Ex 7 |

TABLE

| Example | 1 | 2 | 3 | 4 | 5 | 6 | 7 |
|---|---|---|---|---|---|---|---|
| Reaction Mixture | | | | | | | |
| Solvent - mls | 200 | 100 | 100 | 100 | 100 | 100 | 100 |
| DPM - moles | 0.2 | 0.1 | 0.1 | 0.1 | 0.1 | 0.1 | 0.1 |
| HBr - moles | 0.6 | 0.2 | 0.15 | 0.2 | 0.2 | 0.2 | 0.2 |
| ratio HBr:DPM | 3 | 2 | 1.5 | 2 | 2 | 2 | 2 |
| ratio $H_2O_2$:DPM | 3.2 | 2.2 | 2.0 | 2.2 | 2.2 | 2.2 | 2.2 |
| Reaction Conditions | | | | | | | |
| Temp °C. | 60 | 60 | 60 | 60 | 60 | 60 | 60 |
| Period - hours | 2.75 | 1.5 | 1.5 | 1.5 | 1.5 | 1.5 | 1.5 |
| Reaction Product | | | | | | | |
| conversion DPM % | 100 | 100 | 100 | 100 | 100 | 100 | 100 |
| Yield ketone % | 96 | 98 | 87 | 93 | 93 | 78 | 84 |
| Selectivity to ketone % | 96 | 98 | 87 | 93 | 93 | 78 | 84 |
| Selectivity to bromo-DPM % | not measured | | | | | | |

| Example | 8 | 9 | CA | CB | CC | M10 | M11 |
|---|---|---|---|---|---|---|---|
| Reaction Mixture | | | | | | | |
| Solvent - mls | 100 | 100 | 100 | 100 | 100 | 100 | 100 |
| DPM - moles | 0.1 | 0.1 | 0.1 | 0.2 | 0.1 | 0.2 | 0.2 |
| HBr - moles | 0.125 | 0.2 | 0.2 | 0.2 | 0.1 | 0.2 | 0.2 |
| ratio HBr:DPM | 1.25 | 2 | 2 | 1 | 1 | 1 | 1 |
| ratio $H_2O_2$: DPM | 2.2 | 2.2 | 2.2 | 1.65 | 2.2 | 1.1 | 1.1 |
| Reaction Conditions | | | | | | | |
| Temp °C. | 60 | 30 | 60 | 60 | 60 | 60 | 30 |
| Period - hours | 1.5 | 2.3 | 3.5 | 1.3 | 1.5 | 1 | 1.35 |
| Reaction Product | | | | | | | |
| conversion DPM % | 100 | 100 | 10 | 95 | 100 | 96 | 95 |
| Yield ketone % | 93 | 90 | 7.7 | 56 | 59 | 9.5 | 5.4 |
| Selectivity | 93 | 90 | 75 | 59 | 59 | 10 | 5 |

TABLE-continued

| | | | | | | | |
|---|---|---|---|---|---|---|---|
| to ketone % | | | | | | | |
| Selectivity to bromoDPM % | nm | nm | nm | 35 | nm | 88 | 95 |

From the Table above, it can be seen very readily that the invention process was able to achieve quantitative conversion of a range of diphenyl methane compounds, and that especially good, i.e. very selective results were achieved starting with diphenylmethane itself and those related compounds in which both of the phenyl groups were substituted in the para (4) position by a halo group, an outstanding result of 98% selectivity being achieved with di(4-fluorophenyl) methane, Ex 2. Even under the less favourable combination of conditions of Ex 3, an extremely good yield of ketone was achieved. The comparison of Examples 2 and 3 shows that the actual amount of HBr as well as the amount of $H_2O_2$ is of some importance in optimising conditions. Secondly, it can also be seen that asymmetrical starting materials can be converted to the ketone with high selectivity, but that slightly more forcing conditions would be advantageous.

Example 8 shows that even a small excess of HBr above an equimolar ratio with the substrate can result in a highly selective conversion to the ketone product, and Example 9 demonstrates that such selectivity is enhanced at reaction temperatures at the higher end of the range specified in the text hereinbefore and slightly impaired at temperatures in the lower part of the range.

Comparison CA demonstrates that in the absence of irradiation the extent of conversion of the diphenyl methane compound is drastically reduced even if substantially longer reaction periods are employed.

Comparisons CB and CC demonstrate that in order to achieve selective production of the ketone, it is necessary to employ at least a slight excess of bromide above an equimolar ratio with the diphenylmethane substrate, otherwise a substantial proportion of the reaction product comprises a bromide-substituted product even if excess hydrogen peroxide is used. This can be seen most clearly by contrasting Example 8, in which the HBr:substrate ratio was 1.25:1 and comparison CC in which the ratio was 1:1, which otherwise were carried out under the same conditions. Examples M10 and M11 demonstrate that under conditions of limited addition of HBr and hydrogen peroxide, the reaction process is confined predominantly to the mono-bromo substitution reaction of the methylene group.

In a further comparison, CD, the procedure of Example 5 was repeated, but employing 1,2-diphenylethane as substrate instead of 4-phenyldiphenyl methane. In this substrate, there are two methylene groups forming the bridge between the phenyl groups, and the end result is a product comprising 83% dibromosubstituted diphenylethane, most probably each of the methylene groups being substituted by a bromo group. There was no detectable ketone formed. The paper by Robinson and Vernon to which reference has previously been made herein suggested the formation of 23.7% of the ketone in 96.5% conversion of 1,2-diphenylethane, using photolysis with bromine and oxygen. This demonstrates that photolysis of diphenyl-substituted alkyl compounds with hydrogen peroxide and HBr produces different results and hence procedes differently from photolysis with bromine added as such and oxygen, even though the similarities between the processes would lead the skilled person to expect to achieve similar results.

The examples of the modified process, M10 and M11 demonstrate that by using a substantially lower ratio of HBr to DPM it is possible to obtain with a high degree of selectivity the product in which the substituted methane group is further substituted by a single bromide group compared with production of the corresponding ketone compound. They further demonstrate that such selectivity is enhanced by controlling the temperature of the reaction mixture to around 30° C. compared with using a temperature in excess of 50° C.

We claim:

1. A process for the oxidation of a diphenyl methane to the corresponding benzophenone in which process a diphenyl methane compound in a reaction medium which includes an organic phase comprising a hydrophobic organic solvent is reacted with bromine whilst irradiating with light of a sufficiently short wavelength to generate bromine radicals from the bromine, wherein
   (a) the diphenyl methane compound is selected from compounds having the general formula:

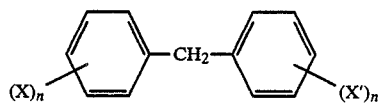

in which each of X and X' represents independently a halogen or sulpho or nitro group or a phenyl group, and n and n' each is an integer from 0 to 3,
   (b) the reaction medium comprises an aqueous phase in addition to the organic phase, said aqueous phase containing HBr and $H_2O_2$ at concentrations sufficient to react to generate bromine in solution in said aqueous phase,
   (c) the amount of HBr present is greater than equimolar to the said diphenyl methane compound, and
   (d) the total amount of hydrogen peroxide reacted in the reaction medium is at least approximately 1.5 moles per mole of the said diphenyl methane compound.

2. A process according to claim 1 wherein the diphenyl methane is unsubstituted or n and/or n' in the formula is 1.

3. A process for the conversion of a diphenyl methane according to claim 2 wherein said hydrogen peroxide is progressively introduced into said reaction medium and wherein the amount of HBr and the total amount of hydrogen peroxide that is introduced into the reaction medium and consumed therein are each approximately equimolar to the diphenyl methane, whereby the diphenyl methane compound is converted mainly to the corresponding diphenyl bromomethane compound.

4. A process according to either claim 1 or 2 wherein either X or X' or both X and X' in the formula represents a group selected from fluoro and chloro groups.

5. A process for the conversion of a diphenyl methane according to claim 4 wherein said hydrogen peroxide is progressively introduced into said reaction medium and wherein the amount of HBr and the total amount of hydrogen peroxide that is introduced into the reaction medium and consumed therein are each approximately equimolar to the diphenyl methane, whereby the diphenyl methane compound is converted mainly to the corresponding diphenyl bromomethane compound.

6. A process according to claim 4 characterised in that the substituent X or X' is or both substituents X and X' are para to the methylene group.

7. A process according to claim 6 wherein the mole ratio of HBr:diphenyl methane is 2:1 to 3:1.

8. A process for the conversion of a diphenyl methane according to claim 6 wherein said hydrogen peroxide is progressively introduced into said reaction medium and wherein the amount of HBr and the total amount of hydrogen peroxide that is introduced into the reaction medium and consumed therein are each approximately equimolar to the diphenyl methane, whereby the diphenyl methane compound is converted mainly to the corresponding diphenyl bromomethane compound.

9. A process according to claim 1 wherein the diphenyl methane compound is symmetrical.

10. A process for the conversion of a diphenyl methane according to claim 9 wherein said hydrogen peroxide is progressively introduced into said reaction medium and wherein the amount of HBr and the total amount of hydrogen peroxide that is introduced into the reaction medium and consumed therein are each approximately equimolar to the diphenyl methane, whereby the diphenyl methane compound is converted mainly to the corresponding diphenyl bromomethane compound.

11. A process according to claim 1 wherein the mole ratio of HBr to diphenyl methane is at least 1.2:1.

12. A process according to claim 1 wherein the mole ratio of hydrogen peroxide:diphenyl methane is from 2:1 to 2.5:1.

13. A process according to claim 1 wherein the hydrogen peroxide is introduced into the reaction mixture in the form of an aqueous solution containing 65 to 70% w/w $H_2O_2$.

14. A process according to claim 1 wherein the volume ratio of the organic to aqueous phases is in the range of from 1:1 to 3:1.

15. A process according to claim 1 wherein the concentration of diphenyl methane in the organic phase is from 100 to 300 g/l.

16. A process according to claim 1 wherein the hydrophic organic solvent is selected from chlorinated hydrocarbon solvents having a boiling point of at least 50° C.

17. A process according to claim 1 wherein the reaction is carried out at a temperature of up to 65° C.

18. A process according to claim 1 wherein the reaction medium is illuminated with light having a wavelength of from 600 to 250 nm.

19. A process according to claim 1 wherein the reaction medium is subjected to light exposure in the range of from $1 \times 10^5$ to $5 \times 10^6$ lux hours.

20. A process according to claim 1 wherein the process is carried out from 1 to 3.5 hours.

21. A process according to claim 1 wherein the hydrogen peroxide is progressively introduced into the reaction medium over a time period of from 5 to 60 minutes.

22. A process according to claim 1 which is carried out in a cyclical manner by reusing the aqueous phase containing hydrogen bromide at the end of the reaction.

23. A process according to claim 22 wherein, before reusing the aqueous phase, bromide is restored by contacting the aqueous phase with a further amount of diphenyl methane and hydrogen peroxide.

24. A process for the conversion of a diphenyl methane according to claim 1 wherein said hydrogen peroxide is progressively introduced into said reaction medium and wherein the amount of HBr and the total amount of hydrogen peroxide that is introduced into the reaction medium and consumed therein are approximately equimolar to the diphenyl methane, whereby the diphenyl methane compound is converted mainly to the corresponding diphenyl bromomethane compound.

25. A process according to claim 24 which employs a reaction temperature of from 20° to 35° C.

26. A process according to claim 1 wherein the mole ratio of HBr to diphenyl methane is at least 1.5:1.

27. A process according to claim 1 wherein the reaction is carried at a temperature in the range of from 50° to 65° C.

* * * * *